United States Patent [19]

Bauerle et al.

[11] 4,047,101

[45] Sept. 6, 1977

[54] FILAMENT FOR ALKALI METAL IONIZATION DETECTOR

[75] Inventors: James E. Bauerle, Pittsburgh; William H. Reed, Monroeville; Edgar Berkey, Murrysville, all of Pa.

[73] Assignee: Westinghouse Electric Corporation, Pittsburgh, Pa.

[21] Appl. No.: 647,464

[22] Filed: Jan. 8, 1976

[51] Int. Cl.² ............................................. G01N 27/00
[52] U.S. Cl. ............................... 324/33; 313/346 R; 313/345
[58] Field of Search ............... 313/345, 346, 355; 324/33; 250/424

[56] References Cited

U.S. PATENT DOCUMENTS

| | | | |
|---|---|---|---|
| 3,116,981 | 1/1964 | Sayre | 313/355 X |
| 3,159,461 | 12/1964 | MacNain | 313/346 DC X |
| 3,170,772 | 2/1965 | Sato et al. | 313/346 X |
| 3,656,020 | 4/1972 | Cronin | 313/346 DC |
| 3,760,212 | 9/1973 | Mennenga | 324/33 |
| 3,760,218 | 9/1973 | Cronin | 313/346 R |
| 3,908,252 | 9/1975 | Willems | 313/346 X |

*Primary Examiner*—Rudolph V. Rolinec
*Assistant Examiner*—Vincent J. Sunderdick
*Attorney, Agent, or Firm*—M. P. Lynch

[57] ABSTRACT

An oxide coated filament exhibiting surface ionization and electron conductivity characteristics is employed in alkali metal ionization detectors to provide extended filament operating life.

8 Claims, 4 Drawing Figures

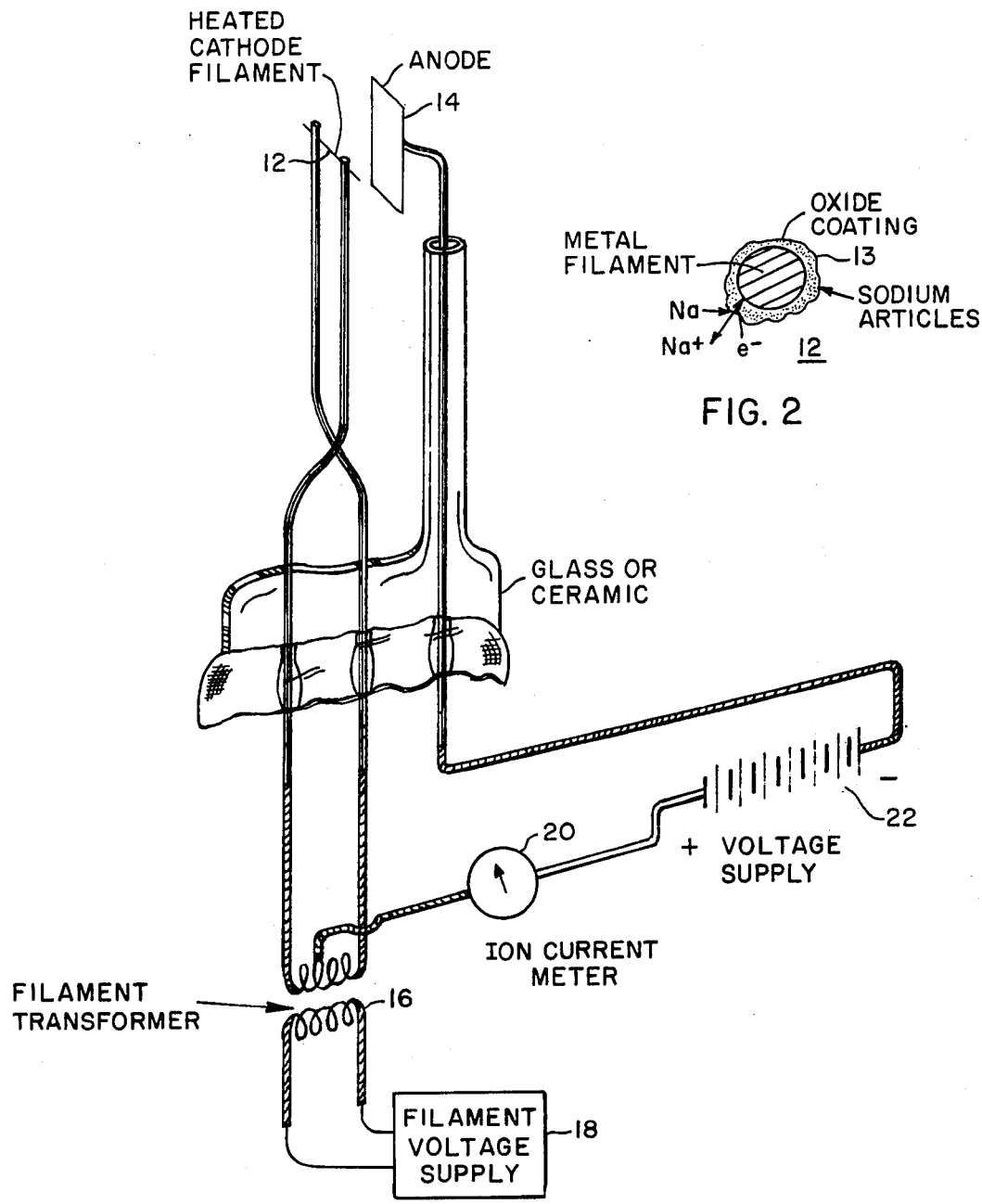

FILAMENT FOR ALKALI METAL IONIZATION DETECTOR

BACKGROUND OF THE INVENTION

Conventional alkali metal ionization detectors, such as those used to monitor sodium, potassium, lithium, etc., operate in vacuum and employ pure metal vacuum filaments and strive to minimize or avoid surface oxidation which has been considered to be detrimental to the useful operation of the detector filaments. Typical vacuum filament material used in alkali metal ionization detectors includes thoria-coated iridium, tungsten, platinum and rhodium. In alkali metal ionization detectors, such as that disclosed in U.S. Patent application Ser. No. 435,389, filed Jan. 21, 1974, entitled "Sensor For Thermally Ionizable Particles And/Or Vapors," which is assigned to the assignee of the present invention and incorporated herein by reference, the detector operating principle consists essentially of thermally ionizing particles or vapors contacting a heated filament to produce ions which are attracted to a collector electrode via an electric field thus producing a current flow which is an indication of the concentration of particles or vapors from which the ions were formed. One of the major considerations in selecting the material composition for the heated filament for conventional alkali metal ionization detectors has been the material's capability of serving as an electron conductor free of surface oxidation which would form an insulator coating thereby ostensibly reducing the effectiveness of the filament. While standard vacuum filament materials such as tungsten, platinum and platinum-rhodium, have operated satisfactorily in vacuum-type ionization detectors, the use of these conventional filament materials in alkali metal ionization detectors operating in environments containing oxygen and at pressures above vacuum, such as atmospheric pressure, have proven unsatisfactory due to the drastic reduction in filament operating life.

There is described herein with reference to the accompanying drawings the use of heating element material as a filament in an alkali metal ionization detector which to produce an alkali metal ionization detector capable of operating satisfactorily over an extended period of time in both an oxygen environment at pressures above or below atmospheric pressure, and a vacuum environment. This eliminates the critical requirement for the vacuum conditions of conventional alkali metal ionization detectors. An oxide coating is developed at the surface of the heating element material to produce a useful filament capable of supporting surface ionization and electron conductivity and having an operating life exceeding that offered by conventional filament materials.

SUMMARY OF THE INVENTION

There is disclosed herein with reference to the accompanying drawings a technique for utilizing conventional furnace heating element materials such as nichrome, Kanthal A alloys, super Kanthal alloys, the latter two being products of the Kanthal Corporation, as well as nickel-chromium-iron alloys, silicon carbide, iron-chromium-aluminum alloys and molybdenum disilicide for the filaments of alkali metal ionization detectors. Oxide coatings are developed on the surface of the heating element material to produce an improved filament material which is substituted for conventional vacuum filaments for use in alkali metal ionization detectors operating in vacuum or in oxygen-containing environments at above vacuum pressures, including atmospheric pressure.

It has been determined through detailed experimental analysis of sodium ionization detectors employing oxide coated heated filaments constructed from conventional heating element material, that an alkali metal ionization detector can be developed for use in atmospheric pressure conditions without encountering the reduction in operating life of the filament which was observed during evaluation of alkali metal ionization detectors employing conventional pure metal vacuum filaments.

A common belief that alkali metals would form stable compounds with an oxide, such that the ion formation and emission required for operation of the alkali metal ionization detector would not occur, has been dispelled by detailed studies of sodium ionization detectors employing oxide-coated filaments of typical heating element material operating in atmospheric conditions. These studies further indicate that the oxide coating of such materials does in fact support good electronic conductivity and that the oxide coating does not significantly limit the electron transfer as has been traditionally assumed.

BRIEF DESCRIPTION OF THE DRAWINGS

The invention will become more readily apparent from the following exemplary description in connection with the accompanying drawings:

FIG. 1 is a schematic illustration of the typical embodiment of an alkali metal ionization detector;

FIG. 2 is a section illustration of an oxide-coated filament or thermal ionizer electrode for use in the embodiment of FIG. 1;

DESCRIPTION OF THE PREFERRED EMBODIMENT

Figure 3:
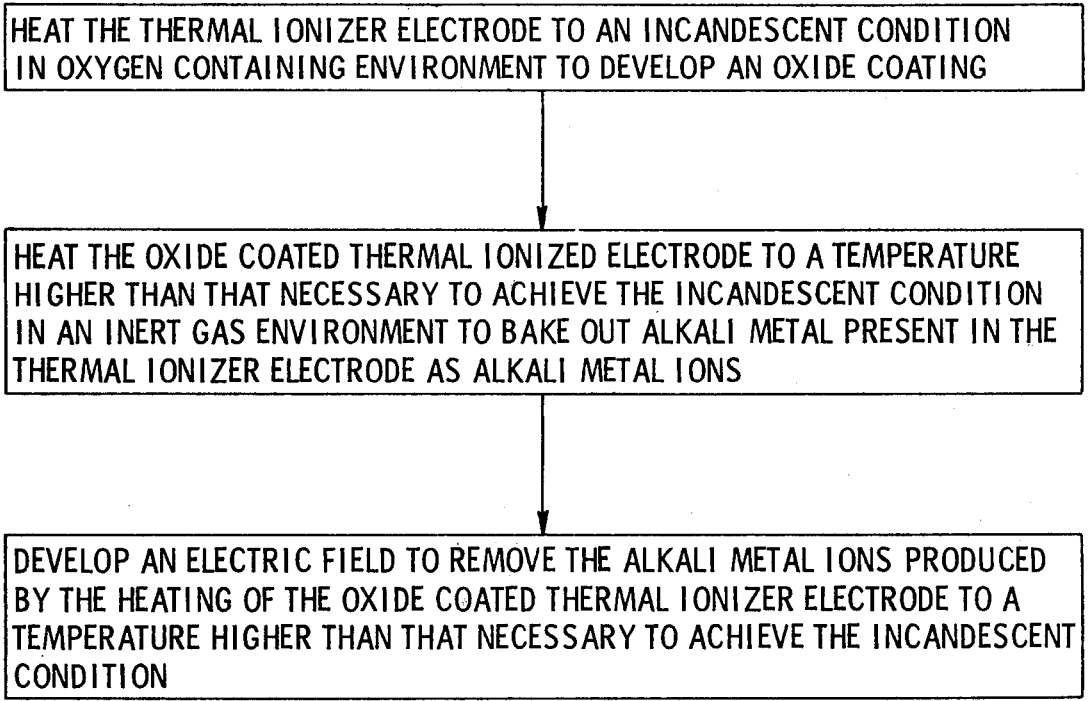
FIG. 3 is a listing of process steps to produce the oxide-coated thermal ionizer electrode or filament.

While the following disclosure has general application to alkali metal ionization detectors operating in an oxygen-containing environment at pressures above vacuum including atmospheric conditions, the discussion for the purposes of clarity, will be directed in particular to a sodium ionization detector, inasmuch as such a device is of particular current interest for monitoring sodium coolant systems such as those used in the fast breeder nuclear reactors.

The sodium ionization detector, as is typically illustrated in FIG. 1, employs a heated filament, or thermal ionizer electrode, which responds to impinging sodium atoms or sodium-containing compounds (vapor or aerosol) to form positive sodium ions which are attracted to a collector electrode via an electric field to produce an ion current which is an indication of the sodium concentration of the environment to which the heated filament is exposed.

Referring to FIG. 1, a typical embodiment of an alkali metal ionization detector 10 is illustrated as consisting of a heated cathode filament 12, also hereinafter functionally referred to as a thermal ionizer electrode, a collector anode 14, a filament transformer 16 for coupling filament voltage supply 18 to heat the cathode filament 12, an ion current meter 20 to indicate the ion current flow between the cathode filament 12 and the anode collector 14 which is maintained by an electric field produced by the voltage supply 22 which is connected between the cathode filament 12 and the anode collector 14. The embodiment of FIG. 1 is described in detail in the above referenced pending U.S. patent application.

Sodium particles, whether contained in a vapor, aerosol or sodium compound, transported by a carrier gas such as flowing air to the vicinity of the detector 10, are converted to free sodium ions at the surface of the heated cathode filament 12 which functions as a thermal ionizer. These ions are then collected by the collector anode 14 which is maintained at a negative potential relative to the heated cathode filament 12 by the voltage source 22. The flow of ions thus established produces an ion current which is measured by the ion current meter 20 as an indication of the concentration of sodium ions present in the environment adjacent to the heated cathode filament 12. The process by which the sodium particles are converted to free sodium ions can be thought of as occurring in the following steps:

1. The collision of sodium particles with the surface of the heated cathode filament 12 and their subsequent melting;
2. The rapid surface diffusion of the melted sodium over the heated cathode filament 12 to form a layer of adsorbed sodium atoms;
3. The transfer of valence electrons from some of the adsorbed sodium atoms to the heated cathode filament 12, converting them to adsorbed sodium ions; and
4. The desorption of the sodium ions from the surface to become free ions, as well as the desorption of neutral sodium ions.

The free sodium ions thus generated contribute to the ion current monitored by the ion current meter 20.

While the use of traditional filament materials, such as platinum, platinum-rhodium and tungsten, etc. have operated satisfactorily in vacuum environments, the useful life of such materials has been significantly reduced when used in alkali metal ionization detectors designed to operate in oxygen environments at pressures above vacuum as would be encountered in a flowing air system.

It has been determined experimentally that materials typically used for heating elements in furnace applications, if processed properly, can produce a filament not only capable of functioning to thermally ionize alkali metal atoms in accordance with the above steps, but can provide a significantly longer operating life than that available from conventional vacuum filament materials when operating in oxygen environments at pressures above vacuum. The superior operation of the heating element materials such as nichrome, Kanthal A, and super Kanthal is attributed to the formation of an oxide coating 13 on the surface of the heating element material, as illustrated in FIG. 2, which acts as a protective filament coating, thus increasing the operating life of the material in non-vacuum conditions, while supporting the necessary surface ionization and electron conductivity required of the heated cathode element 12 of an alkali metal ionization detector of the type illustrated in FIG. 1. The protective oxide coating 13 developed on the surface of the heating element materials when subjected to elevated detector operating temperatures, reduces the vaporization of the underlying metal and thus protects it from rapid oxidation. Such oxide-protected heating element materials, when employed as the heated cathode filaments of an alkali metal ionization detector, support the necessary operation of the alkali metal ionization detector as listed above while further providing operating lifetimes significantly longer than those achieved with the traditional pure metal vacuum filament electrode materials when operating in an oxygen environment.

Three specific oxide-protected filaments tested include chromium oxide, aluminum oxide and silicon dioxide-protected filaments. The aluminum oxide-protected filament is achieved by temperatures cycling Kanthal A which is an alloy of iron, chromium and aluminum to a first temperature level of approximately 1100°–1200° C to produce an aluminum oxide ($Al_2O_3$) coating and to yet a higher temperature to bake out alkali metal impurities in accordance with the process steps of FIG. 3. Typically this temperature cycling occurs with the filament secured within a detector embodiment such as that illustrated in FIG. 1 through the use of the filament voltage supply 18. The electric field established by the supply voltage 22 functions to remove the alkali metals produced during the bake-out of the filament. While the temperature cycling could be accomplished by inserting the filament in an oven, the oven heating elements would tend to generate more alkali metal impurities than would be removed from the filament.

Corresponding temperature cycling of super Kanthal, which consists of a binder, such as clay, and molydisilicide ($MoSi_2$) produces a silicon dioxide protected filament while temperature cycling of a nichrome heating element, which is an alloy of nickel and chromium, will produce a chromium oxide protected filament suitable for use in an alkali metal ionization detector operating in atmospheric conditions.

The following tabulation illustrates the improved filament lifetime achieved with oxide coated filaments in contrast with traditional filament materials represented by thoria-coated iridium and the platinum group represented by platinum-10% rhodium.

| Lifetimes of Filament Materials in Air | | | |
| --- | --- | --- | --- |
| Material | No. Of Filaments | Temperature, °C | Average Life, Hours |
| Thoria-coated iridium | 1 | 1000 | 0.2 |
| Platinum-10% Rhodium | 1 | 1000 | 365 |
| Rhodium | 4 | 1100 | 59 |
| Chromium oxide protected | 2 | 1100 | 526 |
| Chromium oxide protected | 1 | 1000 | 2,324 |
| Aluminum oxide protected | 1 | 1200 | 680 |
| Aluminum oxide protected | 4 | 1100 | 5,024 |
| Silicon dioxide protected | 1 | 1200 | 11,059* |
| Silicon dioxide protected | 1 | 1200 | 10,074* |

*Life tests still in progress, 12/23/75.

The processing steps, as listed in FIG. 3, for super Kanthal to achieve the desired silicon dioxide protected filament consists of:

1. Heating a filament, or thermal ionizer electrode, constructed from super Kanthal in an oxygen environment, i.e. air, at a temperature between 1100° and 1200° C, which corresponds to the incandescent region, for approximately one-half hour to produce the desired silicon dioxide coating, and
2. Heating the silicon dioxide coated filament achieved in step (1) in an inert gas environment, such as nitrogen, at a temperature higher than that of step (1), i.e., 1300°–1400° C, to bake out alkali metal impurities present in the filament.

The corresponding temperature processing of nichrome to achieve a suitable chromium oxide protected nichrome filament consists of steps (1) and (2) above substituting the temperature of approximately 1100° C for step (1) and the temperature range of 1200°–1300° for step (2). These same process parameters will produce an aluminum oxide protective coating on Kanthal A-1.

In addition to the advantages of the silicon dioxide coating of the super Kanthal, the operating temperature for the super Kanthal oxide protected filament is approximately 900° C which is significantly less than the temperature range for producing the oxide coating in accordance with process step 1 which further improves the operating life of the silicon dioxide super Kanthal filament.

Inasmuch as the oxide-coated filaments are derived from conventional heating element materials, such as those identified above, the detector operating temperatures in excess of 700° C required for dissociating sodium atoms from sodium compounds such as sodium hydroxide, in order to appropriately monitor the sodium concentration of a gas, vapor, or aerosol, are well within the temperature capabilities of the heating element material used to construct the filaments for the alkali metal ionization detector 10.

Figure 4:
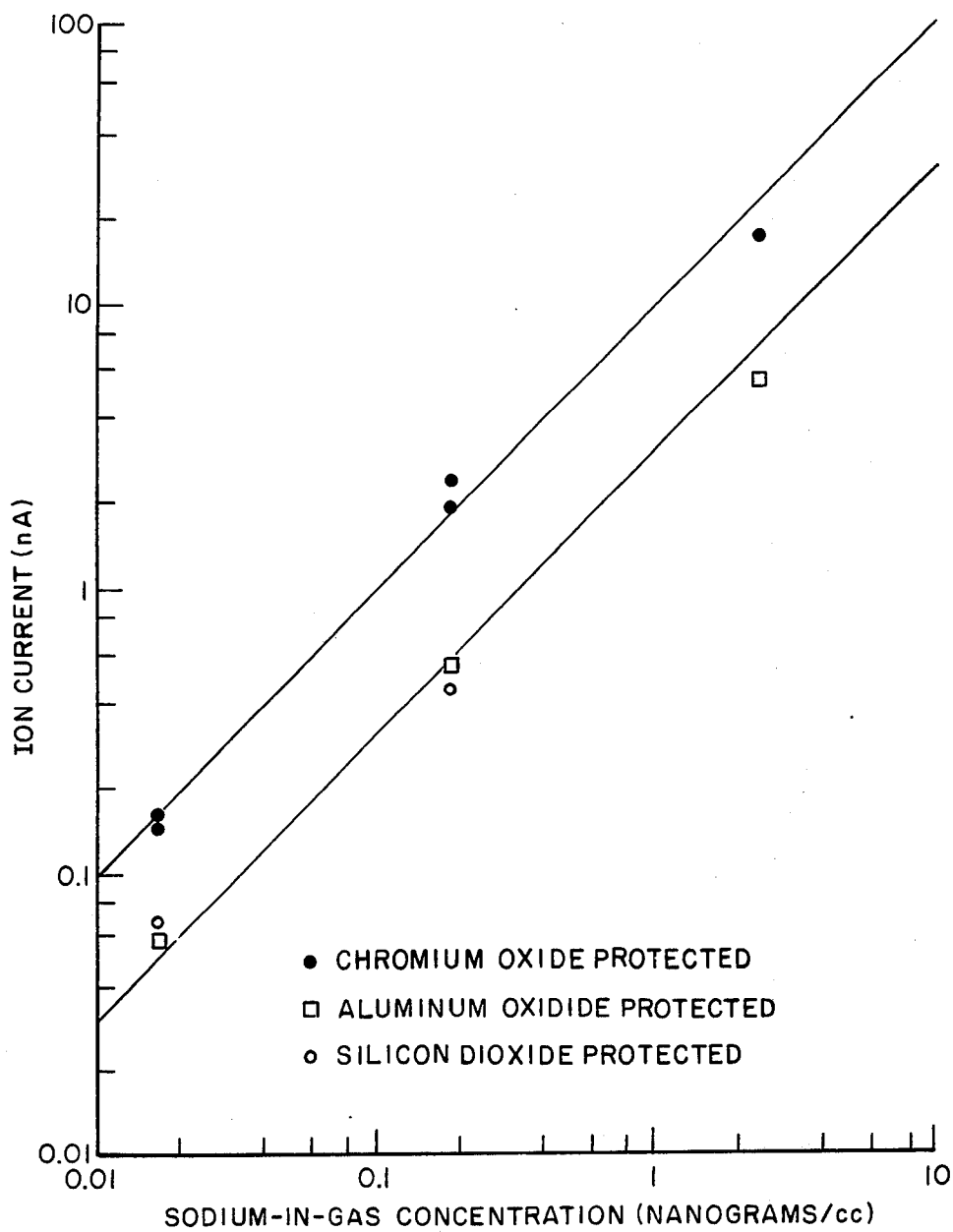
FIG. 4 is a graphical illustration of the operational characteristics of oxide-coated filaments in an embodiment of the invention as illustrated in FIG. 1.

The results of FIG. 4 of filaments constructed in accordance with the above processes, clearly indicates that the oxide coating does in fact support sodium diffusion at rates which render the oxide protected heating element materials most desirable for use in alkali metal ionization detectors.

The sodium diffusion occurring in the oxide coating has been attributed to: (1) the relative thinness of the protective oxide coating; (2) the presence of pores and grain boundaries in the oxide coating; and (3) relatively high diffusion of alkali atoms in the oxide coating by virtue of the relatively small size of the alkali atom.

The section view of a typical oxide-coated heating element material used as the heated cathode filament of an alkali metal ionization detector is illustrated in FIG. 2.

While the above discussion clearly supports the operational status of oxide-coated filaments for alkali metal ionization detectors, the embodiments disclosed by way of example rely on the reaction of the inherent material composition of the filament in an oxygen atmosphere, i.e. air, at eberated temperatures to develop the desired oxide coating. A similar result can also be achieved via a process which deposits a coating of a selected composition on the surface of the filament via any one of several well known techniques such as evaporation in vacuum, cathode sputtering, chemical vapor deposition, chemical solution deposition and ion plating.

Compositions suitable for deposition on a selected filament material to form an oxide coating include metals from which oxides could be formed (chromium, aluminum, silicon, etc.) and the oxides themselves.

We claim as our invention:

1. An alkali metal ionization detector comprising:
   a thermal ionizer means consisting of a first electrode having an oxide protective coating for responding to impinging alkali metal atoms and compounds present in a carrier gas by producing positive alkali metal ions by thermal surface ionization of the alkali metal atoms and compounds,
   first circuit means for maintaining the temperature of said thermal ionizer means at a temperature to ionize said alkali metal atoms and compounds,
   second electrode means, and
   second circuit means for establishing a flow of said positive alkali metal ions from said thermal ionizer means to said second electrode, said flow of positive alkali metal ions being indicative of the concentration of said alkali metal present in said carrier gas.

2. An alkali metal ionization detector as claimed in claim 1 wherein said oxide protective coating supports thermal surface ionization of said alkali metal atoms and compounds at its surface and electron conductivity therethrough to said first electrode.

3. An alkali metal ionization detector as claimed in claim 1 wherein said carrier gas is an oxygen-containing carrier gas.

4. An alkali metal ionization detector as claimed in claim 1 wherein said thermal ionizer means is exposed to atmospheric pressure.

5. An alkali metal ionization detector as claimed in claim 1 wherein said carrier gas contains oxygen and the pressure to which the thermal ionizer means is subjected is above vacuum.

6. An alkali metal ionization detector as claimed in claim 1 wherein said first electrode is constructed of a material from the group consisting of nichrome, Kanthal A and super Kanthal alloys, nickel-chromium-iron alloys, iron-chromium-aluminum alloys, silicon carbide and molybdenum disilicide.

7. An alkali metal ionization detector as claimed in claim 6 wherein said oxide protective coating is an oxide of the material from which the first electrode is constructed.

8. An alkali metal ionization detector as claimed in claim 1 wherein said oxide protective coating is one of the group consisting of chromium oxide, aluminum oxide and silicon dioxide.

* * * * *